(12) United States Patent
Sugiyama (10) Patent No.: US 10,470,697 B2
(45) Date of Patent: Nov. 12, 2019

(54) WAKEFULNESS DETERMINATION METHOD

(71) Applicant: TS TECH CO., LTD., Asaka-shi, Saitama (JP)

(72) Inventor: Shinji Sugiyama, Tochigi (JP)

(73) Assignee: TS Tech Co., Ltd., Saitama (JP)

( * ) Notice: Subject to any disclaimer, the term of this patent is extended or adjusted under 35 U.S.C. 154(b) by 0 days.

(21) Appl. No.: 15/770,622

(22) PCT Filed: Oct. 28, 2016

(86) PCT No.: PCT/JP2016/082036
§ 371 (c)(1),
(2) Date: Apr. 24, 2018

(87) PCT Pub. No.: WO2017/073719
PCT Pub. Date: May 4, 2017

(65) Prior Publication Data
US 2019/0053748 A1 Feb. 21, 2019

(30) Foreign Application Priority Data
Oct. 30, 2015 (JP) .................................. 2015-214731

(51) Int. Cl.
*G08B 23/00* (2006.01)
*A61B 5/18* (2006.01)
(Continued)

(52) U.S. Cl.
CPC .................. *A61B 5/18* (2013.01); *A61B 5/08* (2013.01); *A61B 5/113* (2013.01); *A61B 5/6893* (2013.01);
(Continued)

(58) Field of Classification Search
None
See application file for complete search history.

(56) References Cited

U.S. PATENT DOCUMENTS

2008/0275309 A1* 11/2008 Stivoric ................ A61B 5/411
600/300
2012/0078122 A1 3/2012 Yokoyama et al.
(Continued)

FOREIGN PATENT DOCUMENTS

JP 2015-080521 A 4/2015
WO 2010/143535 A1 12/2010
(Continued)

*Primary Examiner* — Julie B Lieu
(74) *Attorney, Agent, or Firm* — Drinker Biddle & Reath LLP (57) ABSTRACT

The present disclosure provides a wakefulness determination method for accurately determining wakefulness. The wakefulness determination method uses a respiration sensor that obtains respiratory data about respiration of a seated occupant, a calculation unit that calculates the respiratory data obtained from the respiration sensor, and a controller including a determination unit that determines a state of the seated occupant. The wakefulness determination method includes: obtaining, by the respiration sensor, respiratory data of the seated occupant; calculating, by the calculation unit, a degree of change in respiration from the obtained respiratory data; and determining, by the determination unit, wakefulness of the seated occupant by using a Bayesian filter where a probability of occurrence of drowsiness in the seated occupant for the degree of change in respiration is taken as a likelihood and the likelihood is multiplied by a prior probability of occurrence of drowsiness.

6 Claims, 6 Drawing Sheets

(51) Int. Cl.
  *B60W 40/08* (2012.01)
  *A61B 5/08* (2006.01)
  *A61B 5/00* (2006.01)
  *A61B 5/113* (2006.01)
  *B60N 2/00* (2006.01)
  *B60N 2/90* (2018.01)

(52) U.S. Cl.
  CPC .............. *A61B 5/725* (2013.01); *B60N 2/002* (2013.01); *B60W 40/08* (2013.01); *A61B 5/746* (2013.01); *B60N 2/90* (2018.02); *B60N 2002/981* (2018.02); *B60W 2040/0827* (2013.01)

(56) References Cited

U.S. PATENT DOCUMENTS

| | | |
|---|---|---|
| 2013/0021462 A1 | 1/2013 | Kadoya et al. |
| 2014/0330094 A1* | 11/2014 | Pacione ................. A61B 5/411 600/301 |
| 2016/0256096 A1 | 9/2016 | Sugiyama et al. |

FOREIGN PATENT DOCUMENTS

| | | |
|---|---|---|
| WO | 2011/118393 A1 | 9/2011 |
| WO | 2015/060268 A1 | 4/2015 |

\* cited by examiner

WAKEFULNESS DETERMINATION METHOD

CROSS REFERENCE TO RELATED APPLICATIONS

This application is a National Stage Entry application of PCT Application No. PCT/JP2016/082036, filed Oct. 28, 2016, which claims the priority benefit of Japanese Patent Application No. JP 2015-214731, filed Oct. 30, 2015, the contents being incorporated herein by reference.

BACKGROUND

The present disclosure relates to a wakefulness determination method, and particularly to a wakefulness determination method that can accurately determine wakefulness of a person.

Recently, for stably driving a vehicle, it has been necessary to detect a change in a physical condition of a driver. Therefore, various techniques are provided in which various parameters indicating conditions of the driver are detected and calculated to thereby determine a change in a physical condition, in particular, wakefulness of the driver.

For example, Patent Document 1 describes the technique where a pressure signal is detected with a pressure sensor on the basis of a load applied from a person and a respiration interval (RI) and a Respiration root Mean Square Successive Difference (RrMSSD), which are associated with respiratory data of a person, are calculated based on the detected pressure signal to thereby perform wakefulness determination in accordance with changes in values of the RI and the RrMSSD. Specifically, a wakefulness-maintenance apparatus according to Patent Document 1 is configured to determine that drowsiness occurs when an increase of RI and an increase of a predetermine amount of RrMSSD have simultaneously occurred (to determine that the person is in a state of low wakefulness).

According to the technique of Patent Document 1, the wakefulness determination is performed by taking, in particular, RrMSSD as an indicator and thereby momentary variations in RI can be accurately obtained. Therefore, the wakefulness determination can be performed while the influence of vibration noises due to external factors, for example, a situation where a person drives a vehicle, is reduced.

PATENT DOCUMENT 1: JP2015-80521A

However, when a person is in concentration of attention where the person temporarily holds his/her breath or when a person is having a conversation, RI and RrMSSD may simultaneously increase. Therefore, even when the person does not really feel drowsy, the occurrence of drowsiness may be wrongly determined. Also, the relationship between changes in RI and RrMSSD values and a condition where drowsiness occurs depends on characteristics of individuals. Therefore, it is difficult to accurately determine wakefulness. Thus, a technique by which wakefulness of a person can be more accurately determined has been desired.

SUMMARY

The present disclosure is made in view of the above-mentioned problems, and an object of the present disclosure is to provide a wakefulness determination method of highly accurately determining wakefulness. Also, another object of the present disclosure is to determine wakefulness highly accurately while the influence due to characteristics of individuals is reduced.

The above problems are solved by a wakefulness determination method using a respiration sensor that obtains respiratory data variable with respiration of a person, a calculation unit that calculates the respiratory data obtained from the respiration sensor, and a controller including a determination unit that determines a state of the person, the wakefulness determination method including: a respiratory data obtaining step in which the respiration sensor obtains the respiratory data of the person; a calculation step in which the calculation unit calculates by computation the degree of change in respiration, which is the degree of change in the obtained respiratory data per unit time; and a wakefulness determination step in which the determination unit determines wakefulness of the person by using a Bayesian filter where a probability of occurrence of drowsiness in the person for the degree of change in respiration is taken as a likelihood and the likelihood is multiplied by a prior probability of occurrence of drowsiness.

According to the above configuration, the Bayesian filter where the probability of occurrence of drowsiness in the person for the degree of change in respiration is taken as the likelihood is used; thereby, when RI and RrMSSD has simultaneously increased, the wakefulness determination can be prevented from being wrongly made and the wakefulness determination method that highly accurately determines wakefulness can be provided.

Also, in the wakefulness determination method of the present disclosure, the method may use an obtaining unit that obtains a wakefulness signal, which is associated with the wakefulness of the person, in reaction to operation by the person, and a storage unit that stores the wakefulness signal sent from the obtaining unit and various conditions at the time of the operation, and in the calculation step, the calculation unit may set the likelihood or the prior probability on the basis of data stored in the storage unit. According to the above configuration, the determination criteria can be adjusted by the operation by the person; therefore, the influence due to characteristics of individuals is reduced and the accuracy of the wakefulness determination can be further increased.

Further, in the wakefulness determination method of the present disclosure, in the calculation step, the calculation unit may calculate by computation a pattern associated with the number of times that the degree of change in respiration has decreased in a predetermined time period, and the likelihood may include a probability of occurrence of drowsiness in the person for the pattern. According to the above configuration, for the pattern associated with the number of times that the degree of change in respiration has decreased in the predetermined time period, the likelihood includes the probability of occurrence of drowsiness in the person; thereby, the influence due to characteristics of individuals is reduced and the accuracy of the wakefulness determination can be further increased.

Furthermore, in the wakefulness determination method of the present disclosure, in the calculation step, the calculation unit may calculate by computation a respiration interval (RI), which is an interval for one respiration of the person, from the respiratory data obtained from the respiration sensor, and the likelihood may include a probability of occurrence of drowsiness in the person for the RI. According to the above configuration, the likelihood includes the probability of occurrence of drowsiness in the person for a value indicating the respiration interval of the person; thereby, the accuracy of the wakefulness determination can be increased.

Moreover, in the wakefulness determination method of the present disclosure, the controller may include a waveform generation unit that generates a respiration interval (RI) waveform data for a respiratory waveform obtained from the respiration sensor. The RI waveform data indicates transitions in a predetermined time period of a respiration interval (RI) that is an interval for one respiration of the person. In a case where a Respiration root Mean Square Successive Difference (RrMSSD) is defined by the following formula 1, $$RrMSSD = \sqrt{\frac{\{RI(t) - RI(t-1)\}^2 + \cdots + \{RI(t+n-1) - RI(t+n-2)\}^2}{n}}$$ [Formula 1]

where the t-th RI in the RI waveform data generated by the waveform generation unit is determined as RI (t) and the n-th RI after the t-th RI in the generated RI waveform data is defined as RI (t+n), in the calculation step, the calculation unit may calculate by computation the RrMSSD from the RI waveform data, and the likelihood may include a probability of occurrence of drowsiness in the person for the RrMSSD. According to the above configuration, the likelihood includes the probability of occurrence of drowsiness in the person for the RrMSSD; thereby, the accuracy of the wakefulness determination can be increased.

Also, in the wakefulness determination method of the present disclosure, the likelihood may include five or six pieces of data. According to the above configuration, if the amount of data configuring the likelihood includes five or six pieces of data, the accuracy of the wakefulness determination can be increased while an increase in load associated with the wakefulness determination processing is inhibited.

According to the present disclosure, the wakefulness determination can be prevented from being wrongly made, and the wakefulness determination method of highly accurately determining wakefulness can be provided. Further, according to the present disclosure, the influence due to characteristics of individuals is reduced and the accuracy of the wakefulness determination can be further increased. Furthermore, according to the present disclosure, the accuracy of the wakefulness determination can be increased while an increase in load associated with the wakefulness determination processing is inhibited.

BRIEF DESCRIPTION OF DRAWINGS

Various embodiments of the invention are illustrated in the drawings, in which.

DETAILED DESCRIPTION

The present disclosure relates to a wakefulness determination method, and particularly to a wakefulness determination method that can highly accurately determine wakefulness of a person. An embodiment to be described below is merely an example for facilitating understanding of the present disclosure and does not limit the present disclosure. In other words, it is understood that shapes, dimensions, and arrangements of components or procedures or the like of a method to be described below can be changed by modification, combination, and so on without departing from the scope of the present disclosure and that the present disclosure may include its equivalents. Hereinafter, a wakefulness determination method according to the embodiment of the present disclosure is concretely described with reference to the attached drawings.

Figure 1:
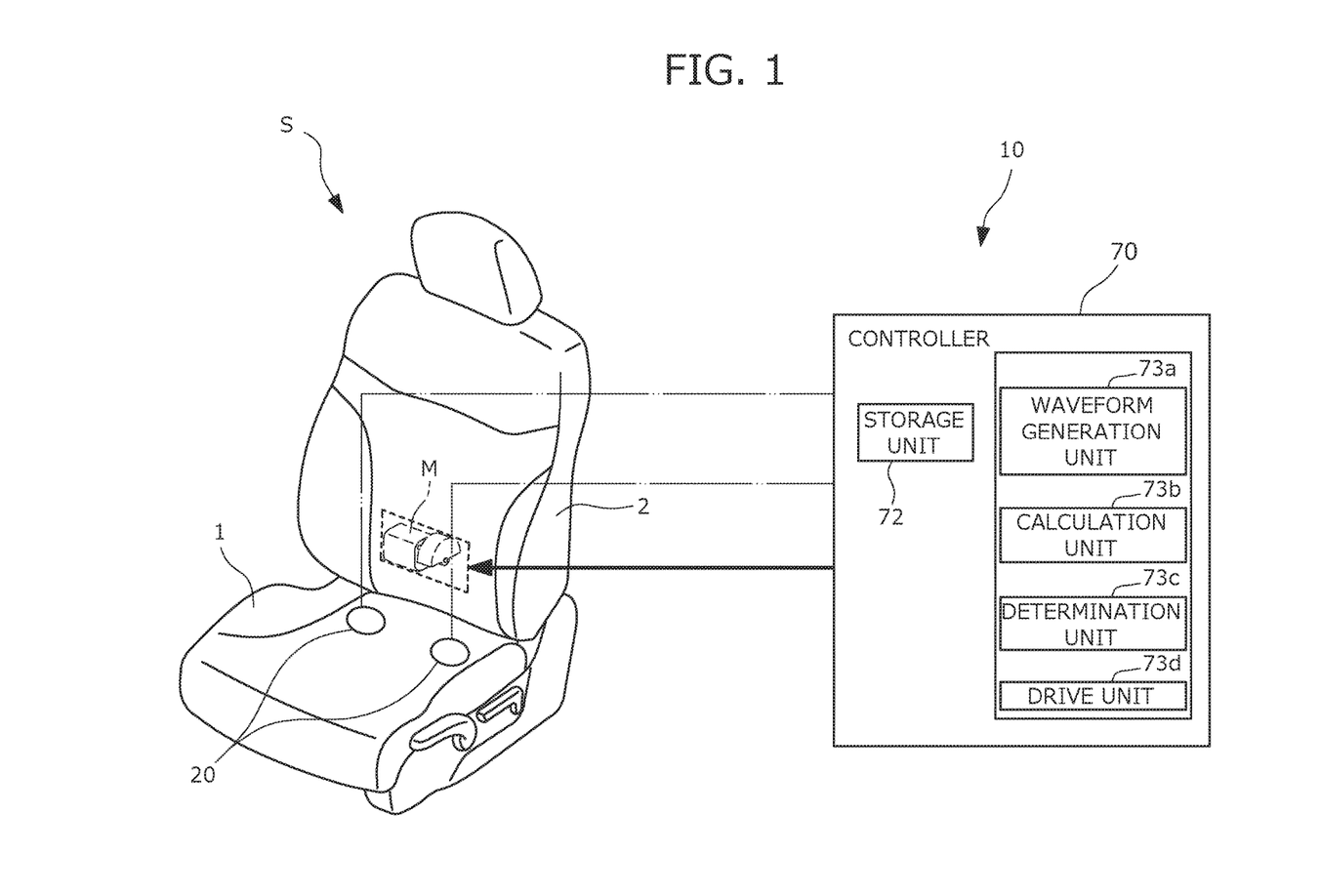
FIG. 1 is a diagram showing the entire configuration of a wakefulness-maintenance apparatus according to an embodiment of the present disclosure.

First, a wakefulness-maintenance apparatus 10 according to the embodiment is described with reference to FIG. 1. Here, FIG. 1 is a drawing showing the entire configuration of the wakefulness-maintenance apparatus 10 according to the embodiment of the present disclosure. The wakefulness-maintenance apparatus 10 according to the embodiment serves to determine wakefulness of a seated occupant as a person on the basis of respiratory data obtained by pressure sensors 20 as respiration sensors. As shown in FIG. 1, the wakefulness-maintenance apparatus 10 mainly includes a vehicle seat S in which the two pressure sensors 20 are arranged within a seat cushion 1 and a vibrating motor M is arranged within a seat back 2, and a controller 70 which is configured to control the pressure sensors 20 and the vibrating motor M.

The vehicle seat S includes the seat cushion 1 at which an occupant is seated and the seat back 2 serving as a backrest for the seated occupant. The pressure sensors 20 are provided within the seat cushion 1 to be positioned adjacent to the seated occupant, and the vibrating motor M is provided within the seat back 2 to be positioned adjacent to the seated occupant.

The pressure sensors 20 each including upper and lower electrodes and a circular detection surface are provided within the seat cushion 1. The pressure sensor 20 is a resistive pressure-sensitive sensor configured to detect electric resistance changing according to respiration of the seated occupant. The electrode on the upper surface of the pressure sensor 20 is deformed downward by pressure applied to the electrode on the upper surface. Accordingly, contact resistance is increased and therefore an electric resistance value between the upper and lower electrodes is decreased. An electric signal associated with the electric resistance value is sent from the pressure sensor 20 to the controller 70 described below. The controller 70 is configured to calculate the pressure on the basis of the electric signal associated with the electric resistance value and to measure respiratory data on the basis of the calculated pressure.

The controller 70 includes a storage unit 72 which is configured with a random access memory (RAM, not shown), a waveform generation unit 73a which is configured to generate voltage waveform data, a calculation unit 73b which is configured to perform data calculation for determining wakefulness, a determination unit 73c which is configured to determine wakefulness, and a drive unit 73d configured to drive the vibrating motor M. These components of the controller 70 function when a program stored on a read-only memory (ROM, not shown) provided in the controller 70 is executed by a central processing unit (CPU, not shown) provided in the controller 70.

The storage unit 72 serves to temporarily store a parameter including signals during control of the calculation and signals to be input and output, and to store other signals such as pressure signals converted to digital signals in the embodiment. On the basis of electric signals associated with resistance values of the pressure sensors 20, which are obtained from the pressure sensors 20 and stored on the storage unit 72, the waveform generation unit 73a functions to generate respiratory data plotted on the vertical axis, respiratory waveform data plotted with time on the horizontal axis, and waveform data calculated from the respiratory waveform data. The calculation unit 73b serves to perform the calculation described below, on the basis of the respiratory waveform data generated by the waveform generation unit 73a. The determination unit 73c serves to perform wakefulness determination by taking the data calculated by the calculation unit 73b as an indicator. The drive unit 73d serves to drive the vibrating motor M in accordance with a determination of a decrease of wakefulness of the seated occupant to stimulate the seated occupant by vibrations. In addition, the functions of the storage unit 72, the waveform generation unit 73a, the calculation unit 73b, the determination unit 73c, and the drive unit 73d is described in detail below.

Wakefulness Determination Processing

Figure 2:
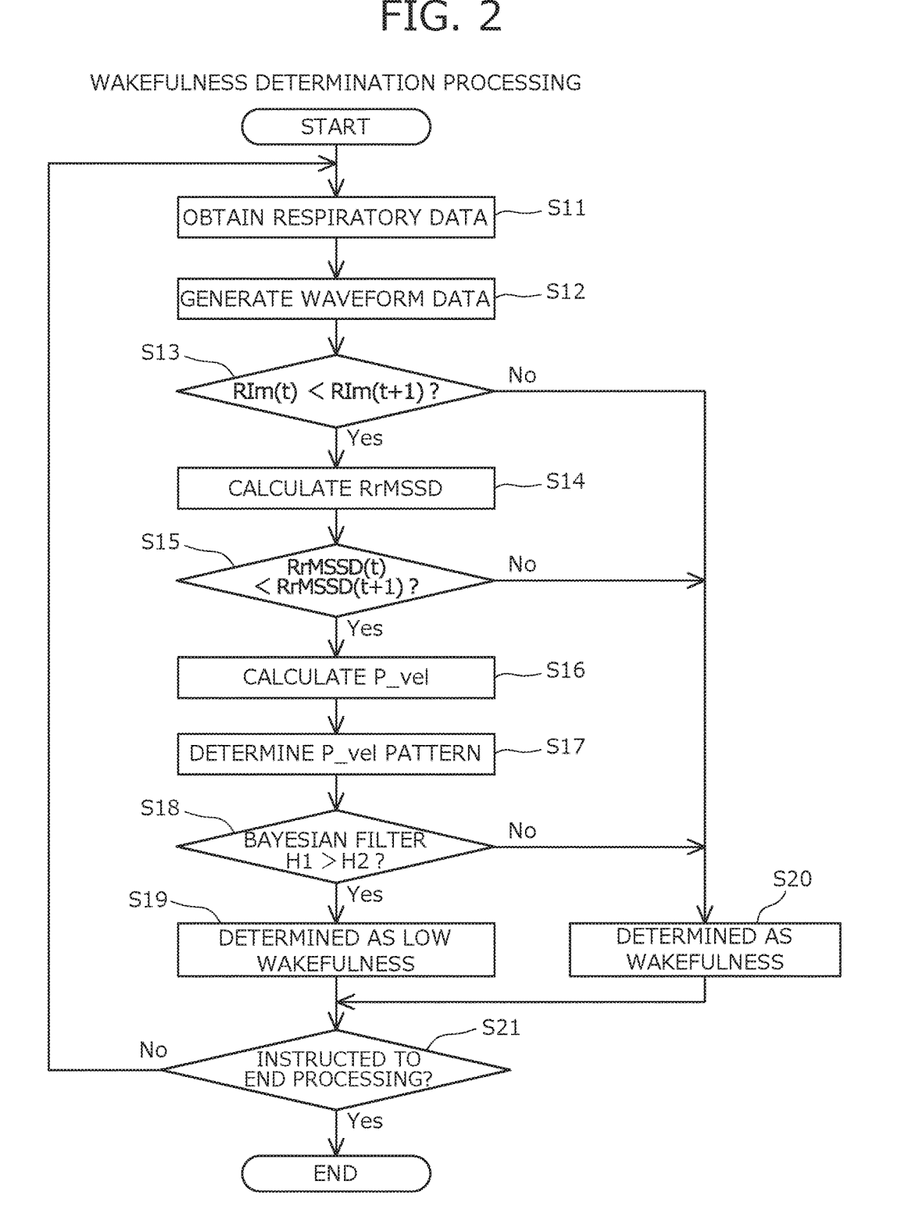
FIG. 2 is a flowchart showing an example of wakefulness determination processing.
Figure 3:
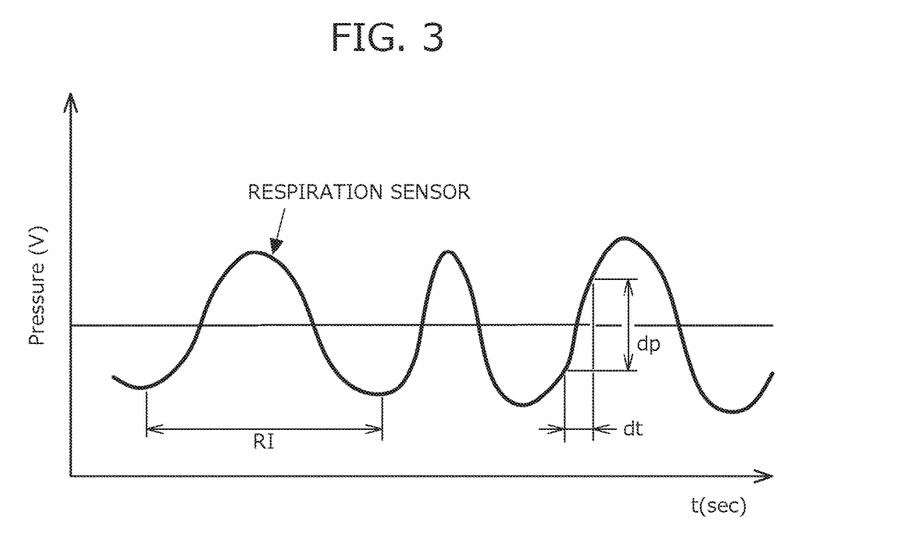
FIG. 3 is a graph showing time-dependent changes in pressure signal.
Figure 4:
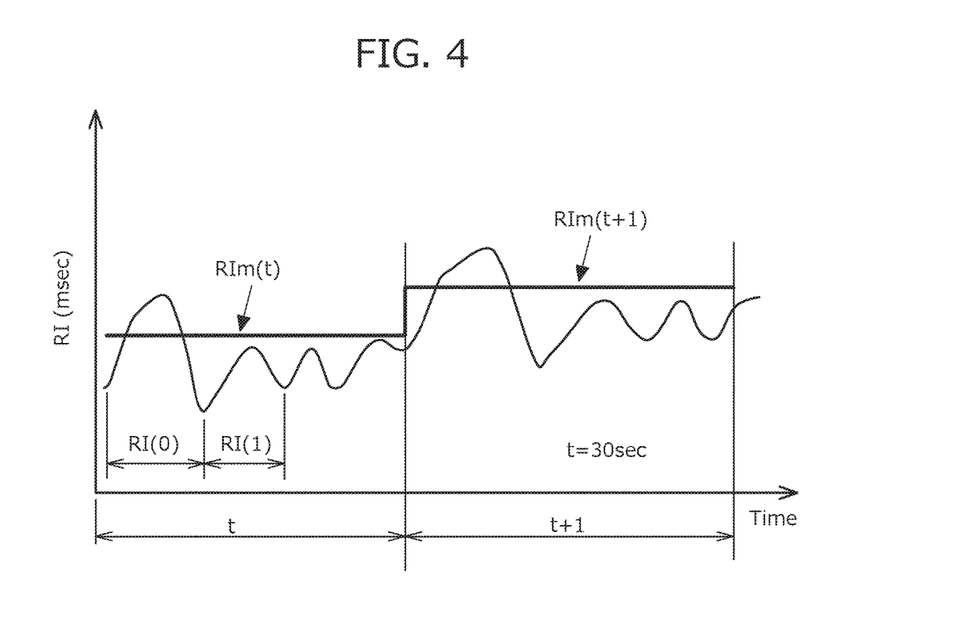
FIG. 4 is a graph showing time-dependent changes in RI and RIm, which is an average value of RI every 30 seconds.
Figure 5:
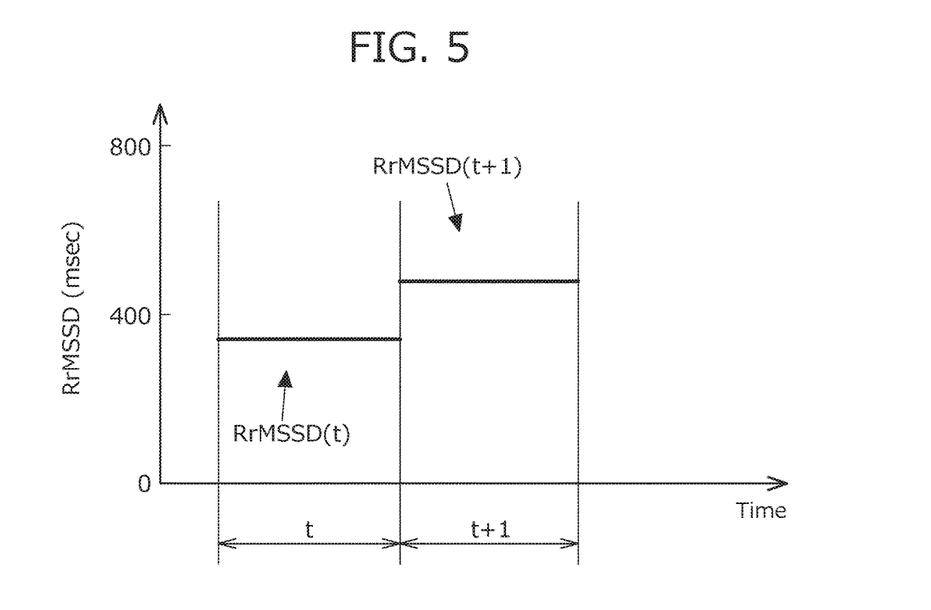
FIG. 5 is a graph showing time-dependent changes in RrMSSD.
Figure 6:
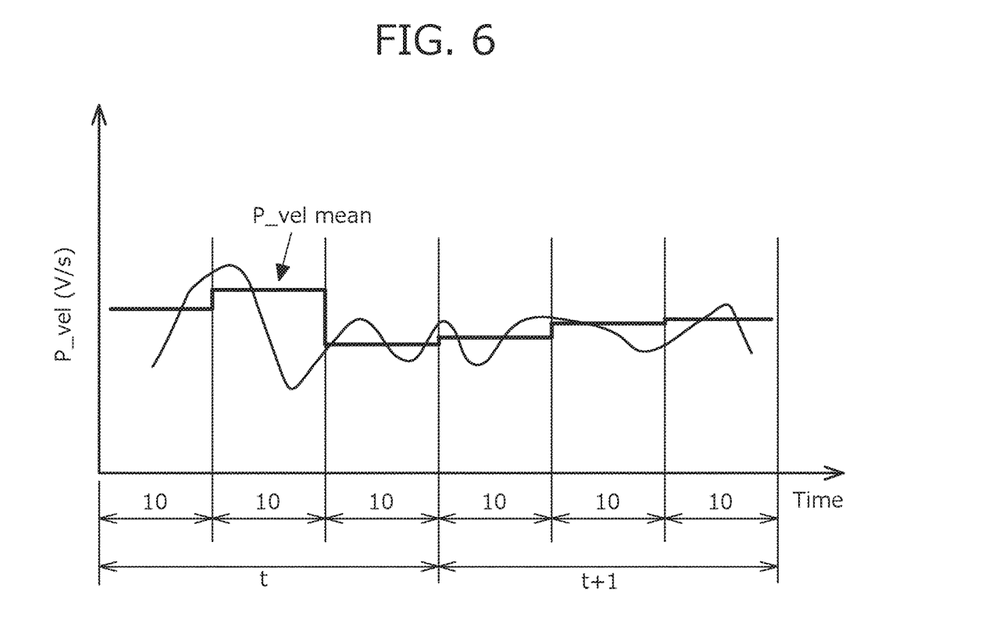
FIG. 6 is a graph showing time-dependent changes in P_vel.
Figure 7:
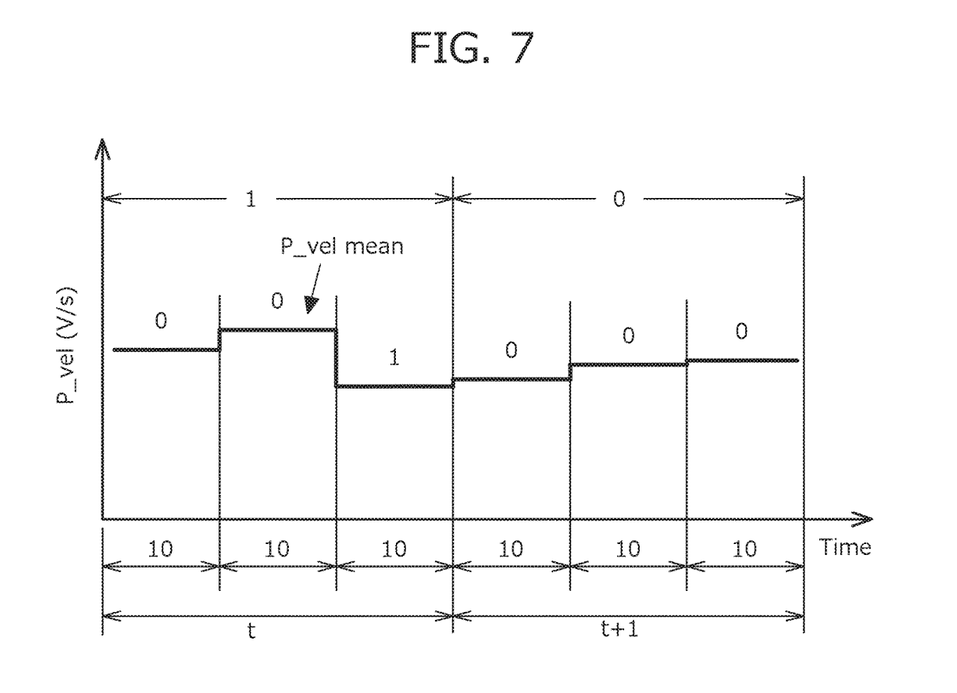
FIG. 7 is a graph showing time-dependent changes in P_vel and illustrating a counting method for making P_vel divided patterns.

Next, the processing details of wakefulness determination processing of the wakefulness-maintenance apparatus 10 configured as described above is described along the flow with reference to FIGS. 2 to 7. FIG. 2 is a flowchart showing an example of the wakefulness determination processing. FIG. 3 is a graph showing time-dependent changes in pressure signal. FIG. 4 is a graph showing time-dependent changes in RI described below and time-dependent changes in RIm, which is an average value of RI every 30 seconds. FIG. 5 is a graph showing time-dependent changes in RrMSSD described below. FIG. 6 is a graph showing time-dependent changes in P_vel described below. FIG. 7 is a graph showing time-dependent changes in P_vel and illustrating a counting method for making P_vel divided patterns described below.

The wakefulness determination processing according to the embodiment is to determine wakefulness of a seated occupant on the basis of a Bayesian filter to which the data or the like associated with RI (Respiration Interval) indicating a respiration interval, RrMSSD (Respiration root Mean Square Successive Difference) described below and indicating variations of RI, and P_vel (Pressure velocity) described below are applied. In addition, for the degree of change in the respiratory data (also referred to as pressure signal) per unit time, the term P_vel is used for convenience in the embodiment.

First, in accordance with starting of an engine of a vehicle or pressing of a start switch (not shown), the pressure sensors 20 obtain respiratory data, which varies according to the depth of respiration of the seated occupant, on the basis of changes in electric resistance. As a respiratory data obtaining step, the pressure sensors 20 obtain the respiratory data of the seated occupant and the controller 70 stores (obtains) the respiratory data sent from the pressure sensors 20 as potential difference data in the storage unit 72 (step S11).

Next, on the basis of the obtained respiratory data in the pressure sensors 20, the waveform generation unit 73a generates pressure waveform data of the respiration sensor illustrated in FIG. 3 as transitions in pressure in a predetermined time period, and RI waveform data illustrated in FIG. 4 as transitions in RI, which is an interval of one respiration of a person, in a predetermined time period (step S12).

Next, in a calculation step, the calculation unit 73b sets intervals each of 30 seconds in the generated RI waveform data as shown in FIG. 4 and calculates an average value RIm of RI within each of the intervals.

Next, the determination unit 73c compares calculated RIm (t) in an interval with RIm (t+1) in an interval subsequent to the previous interval and then determines whether RIm (t+1) is a value greater than RIm (t) in the previous interval (step S13).

Then, in a case where the determination unit 73c has determined that RIm (t+1) is a value smaller than or equal to RIm (t) (step S13: No), the determination unit 73c determines that the seated occupant is in a state of wakefulness (step S20). In a case where the determination unit 73c has determined that RIm (t+1) is a value greater than RIm (t), that is, in a case where a value of RIm has increased in a subsequent interval than that in an interval directly previous to the subsequent interval (step S13: Yes), the calculation unit 73b calculates RrMSSD in the calculation step (step S14). Specifically, the calculation unit 73b sets intervals each of 30 seconds and calculates RrMSSD within each of the intervals. Here, RrMSSD is a value calculated by the following formula 1 where the t-th RI is defined as RI (t) and the n-th RI after the t-th RI is defined as RI (t+n), and RrMSSD indicates variations of RI.

$$RrMSSD = \sqrt{\frac{\{RI(t) - RI(t-1)\}^2 + \cdots + \{RI(t+n-1) - RI(t+n-2)\}^2}{n}}$$ [Formula 1]

RrMSSD increases in the early stage of low wakefulness in accordance with the activation of sympathetic nerves when the seated occupant tries to shake off drowsiness. Thus, this RrMSSD is set as an indicator; thereby, the wakefulness determination is made more accurately.

Next, the determination unit 73c compares calculated RrMSSD (t) in an interval shown in FIG. 5 with RrMSSD (t+1) in an interval subsequent to the previous interval and then determines whether RrMSSD (t+1) is a value greater than RrMSSD (t) in the previous interval (step S15).

Thereafter, in a case where the determination unit 73c has determined that RrMSSD (t+1) is a value smaller than or equal to RrMSSD (t) (step S15: No), the determination unit 73c determines that the seated occupant is in a state of wakefulness (step S20). In a case where the determination unit 73c has determined that RrMSSD (t+1) is a value greater than RrMSSD (t), that is, in a case where a value of RrMSSD has increased in a subsequent interval than that in an interval directly previous to the subsequent interval (step S15: Yes), the calculation unit 73b calculates P_vel shown in FIG. 6 in the calculation step (step S16).

Here, P_vel is the degree of change in the respiratory data (the degree of change in respiration) per unit time as described above. In other words, P_vel is the absolute value of a value obtained by temporal differentiation of the respiratory data obtained in a predetermined time period. In particular, P_vel is a value which has been median filtered and low-pass filtered and from which noise has been removed. In addition, P_vel is data to be applied to a Bayesian filter described below.

Next, in the calculation step, the calculation unit 73b calculates P_vel mean, which an average value of P_vel every 10 seconds and determines, on the basis of P_vel mean, P_vel pattern shown in FIG. 7 and table 1 (step S17).

TABLE 1

| P_vel pattern | | t + 1 | | | |
|---|---|---|---|---|---|
| | | 0 | 1 | 2 | 3 |
| t | 0 | 1 | 2 | 3 | 4 |
| | 1 | 5 | 6 | 7 | 8 |
| | 2 | 9 | 10 | 11 | 12 |
| | 3 | 13 | 14 | 15 | 16 |

This table 1 is to indicate P_vel pattern defined by the number of times that P_vel has decreased during time t and the number of times that P_vel has decreased during time t+1.

As shown in FIG. 7 and table 1, P_vel pattern is a pattern defined by the number of times that P_vel mean has decreased in a predetermined period time. In the embodiment, P_vel pattern includes 16 patters in total. In the embodiment, P_vel pattern is determined by a combination of the number of times that during time t of 30 seconds, P_vel mean has decreased in the subsequent 10 seconds than that in the previous 10 seconds with the number of times that during time t+1 of 30 seconds, P_vel mean has decreased in the subsequent 10 seconds than that in the previous 10 seconds. For example, as shown in FIG. 7, the number of times that P_vel mean has decreased during time t is 1 and the number of times that P_vel mean has decreased during time t+1 is 0. In this case, P_vel pattern is determined as 5 as shown in table 1.

Technically, in terms of the number in the first 10 seconds during time t, P_vel mean in the first 10 seconds during time t is compared with P_vel mean in the previous 10 seconds during time t (not shown). This P_vel pattern is data to be applied to the Bayesian filter described below.

Next, in a wakefulness determination step, the determination unit 73c uses the Bayesian filter including values of RIm, P_vel, and P_vel pattern, which are calculated by the calculation unit 73b, as the data and determines whether a probability that the seated occupant is in a state of low wakefulness (a state where drowsiness occurs) is greater than a probability that the seated occupant is in a state of wakefulness (step S18). Here, the Bayesian filter formula is expressed by formula 2.

$$P(D1|H1) \times P(D2|H1) \times P(D3|H1) \times P(H1) > P(D1|H2) \times P(D2|H2) \times P(D3|H2) \times P(H2) \quad \text{[Formula 2]}$$

As just described, P(D1|H1)×P(D2|H1)×P(D3|H1), i.e., the multiplication of probabilities of wakefulness, which are associated with various data described below, corresponds to a likelihood of the Bayesian filter, and P(D1|H2)×P(D2|H2)×P(D3|H2), i.e., the multiplication of probabilities of wakefulness, which are associated with various data described below, corresponds to a likelihood of the Bayesian filter. In addition, P(H1) and P(H2) are prior probabilities.

Next, the probabilities and the prior probabilities, which are associated with the data to be applied to the Bayesian filter is described in detail.

Probability on Data D1 Associated with RIm

For data D1 corresponding to a value of RIm, probability P(D1|H1) that data D1 can be obtained when the seated occupant is in a state of low wakefulness and probability P(D1|H2) that data D1 can be obtained when the seated occupant is in a state of wakefulness is described with reference to table 2.

TABLE 2

| RIm range | Probability of low wakefulness P (D1|H1) | Probability of wakefulness P (D1|H2) |
|---|---|---|
| 2000 < D1 ≤ 3250 | P11a | P12a |
| 3250 < D1 ≤ 4750 | P11b | P12b |
| 4750 < D1 | P11c | P12c |

As shown in table 2, probability P(D1|H1) that D1 is larger than 2000 and smaller than or equal to 3250 (2000<D1≤3250) when the seated occupant is in a state of low wakefulness is P11a, and probability P(D1|H2) that D1 is larger than 2000 and smaller than or equal to 3250 (2000<D1≤3250) when the seated occupant is in a state of wakefulness is P12a. Also, probability P(D1|H1) that D1 is larger than 3250 and smaller than or equal to 4750 (3250<D1≤4750) when the seated occupant is in a state of low wakefulness is P11b, and probability P(D1|H2) that D1 is larger than 3250 and smaller than or equal to 4750 (3250<D1≤4750) when the seated occupant is in a state of wakefulness is P12b. In addition, probability P(D1|H1) that D1 is larger than 4750 (4750<D1) when the seated occupant is in a state of low wakefulness is P11c, and probability P(D1|H2) that D1 is larger than 4750 (4750<D1) when the seated occupant is in a state of wakefulness is P12c. That is, the sum of P11a, P11b, and P11e and the sum of P12a, P12b, and P12c are each 1. In addition, a database of contents shown in table 2, a database of contents shown in table 3 described below, and a database of contents shown in table 4 described below are stored in advance in the storage unit 72.

Probability on Data D2 Associated with P_vel Mean

For data D2 corresponding to a value of P_vel mean, probability P(D2|H1) that data D2 can be obtained when the seated occupant is in a state of low wakefulness and probability P(D2|H2) that data D2 can be obtained when the seated occupant is in a state of wakefulness is described with reference to table 3.

TABLE 3

| P_vel mean range | Probability of low wakefulness P(D2|H1) | Probability of wakefulness P(D2|H2) |
|---|---|---|
| 0 < D2 ≤ 0.10 | P21a | P22a |
| 0.10 < D2 ≤ 0.22 | P21b | P22b |
| 0.22 < D2 | P21c | P22c |

As shown in table 3, probability P(D2|H1) that D2 is larger than 0 and smaller than or equal to 0.10 (0<D2≤0.10) when the seated occupant is in a state of low wakefulness is P21a, and probability P(D2|H2) that D2 is larger than 0 and smaller than or equal to 0.10 (0<D2≤0.10) when the seated occupant is in a state of wakefulness is P22a. Probability P(D2|H1) that D2 is larger than 0.10 and smaller than or equal to 0.22 (0.10<D2≤0.22) when the seated occupant is in a state of low wakefulness is P21b, and probability P(D2|H2) that D2 is larger than 0.10 and smaller than or equal to 0.22 (0.10<D2≤0.22) when the seated occupant is in a state of wakefulness is P22b. Probability P(D2|H1) that D2 is larger than 0.22 (0.22<D2) when the seated occupant is in a state of low wakefulness is P21c, and probability P(D2|H2) that D2 is larger than 0.22 (0.22<D2) when the seated occupant is in a state of wakefulness is P22c. That is, the sum of P21a, P21b, and P21c and the sum of P22a, P22b, and P22c are each 1.

Probability on Data D3 Associated with P_vel Pattern

For data D3 corresponding to a value of P_vel pattern, probability P(D3|H1) that data D3 can be obtained when the seated occupant is in a state of low wakefulness and probability P(D3|H2) that data D3 can be obtained when the seated occupant is in a state of wakefulness is described with reference to table 4.

TABLE 4

| D3: P_vel pattern | Probability of low wakefulness P(D3|H1) | Probability of wakefulness P(D3|H2) |
|---|---|---|
| 1 | P31a | P32a |
| 2 | P31b | P32b |
| 3 | P31c | P32c |
| 4 | P31d | P32d |
| 5 | P31e | P32e |
| 6 | P31f | P32f |
| 7 | P31g | P32g |
| 8 | P31h | P32h |
| 9 | P31i | P32i |
| 10 | P31j | P32j |
| 11 | P31k | P32k |
| 12 | P31l | P32l |
| 13 | P31m | P32m |
| 14 | P31n | P32n |
| 15 | P31o | P32o |
| 16 | P31p | P32p |

As shown in FIG. 4, probability P(D3|H1) that D3=1, 2 . . . 15, 16 is obtained when the seated occupant is in a state of low wakefulness, is P31a, P31b . . . P31o, P31p in order, and probability P(D3|H2) that D3=1, 2 . . . 15, 16 is obtained when the seated occupant is in a state of wakefulness, is P32a, P32b . . . P32o, P32p in order. That is, the sum of P31a, P31b . . . P31o, P31p and the sum of P32a, P32b . . . P32o, P32p are each 1.

P_vel pattern is different from large and small values of P_vel mean, which depend on characteristics of individuals, and P_vel pattern indicates a constant trend regardless of the characteristics of the individuals. Therefore, P_vel pattern is suitable for determining wakefulness of a person. That is, the Bayesian filter includes (D3|H1), (D3|H2) associated with P_vel pattern in the likelihood; thereby, wakefulness of the seated occupant can be more accurately determined.

Prior Probability

Prior probability P(H1) is a probability that the seated occupant is brought into low wakefulness, and prior probability P(H2) is a probability that the seated occupant is brought into wakefulness. That is, the sum of P(H1) and P(H2) is 1.

(Wakefulness Determination with Bayesian Filter)

When the respective probabilities are substituted into the above formula 2 and formula 2 is established, that is, when a left-side value is larger than a right-side value (step S18: Yes), the determination unit 73c determines in the wakefulness determination step that the seated occupant is in a state of low wakefulness (step S19). When formula 2 is not established, that is, when a left-side value is smaller than or equal to a right-side value (step S18: No), the determination unit 73c determines that the seated occupant is in a state of wakefulness (step S20). For example, when D1=3500, D2=0.15, and D3=7, P(D1|H1)=P11b, P(D1|H2)=P12b, P(D2|H1)=P21b, P(D2|H2)=P22b, P(D3|H1)=P31g, and P(D3|H2)=P32g are obtained as shown in table 5.

TABLE 5

| | Probability of low wakefulness | Probability of wakefulness |
|---|---|---|
| RI | P (D1|H1) = P11b | P (D1|H2) = P12b |
| P_vel | P (D2|H1) = P21b | P (D2|H2) = P22b |
| P_vel pattern | P (D3|H1) = P31g | P (D3|H2) = P32g |
| Prior probability | P (H1) = 0.7 | P (H2) = 0.3 |

In addition, when P(H1)=0.7, P(H2)=0.3, the calculation unit 73b substitutes these values into formula 2 to obtain formula 3 and the determination unit 73c determines whether or not formula 3 is established and whether or not the seated occupant is in a state of wakefulness.

$$P11b \times P21b \times P31g \times 0.7 \square P12b \times P22b \times P32g \times 0.3 \quad \text{[Formula 3]}$$

After determining wakefulness of the seated occupant (step S19, step S20), the controller 70 may indicate a determination result on a display (not shown) installed in a vehicle so that the determination result is informed to a fellow occupant. Also, the controller 70 may perform the wakefulness maintenance processing with the vibrating motor M described below.

Finally, the controller 70 judges whether or not the seated occupant has given a processing termination instruction by pressing a stop switch (not shown) or by another operation (step S21). In a case where there is no instruction (step S21: No), the processing returns to the respiratory data obtaining step of step S11. In a case where the processing termination instruction is given (step S21: Yes), the controller 70 ends the processing.

In addition, an interval of 30 seconds is set for the interval in which RIm as an average value of RI is calculated in step S13 and for the interval in which RrMSSD is calculated in step S14, but not limited thereto. An interval of 20 seconds to 300 seconds may be set. As such an interval is set longer, it takes longer to determine wakefulness; however, the amount of data to be extracted for averaging parameters is increased. Therefore, the reliability of the wakefulness determination is enhanced.

Also, in the embodiment, the range of RIm as data D1, the range of P_vel mean as data D2, and the range of P_vel pattern as data D3, which are applied to the Bayesian filter are each merely an example. In other words, the range may be divided into small ranges or may be expanded. Also, the number of ranges may be increased or decreased.

Wakefulness Maintenance Processing

Figure 8:
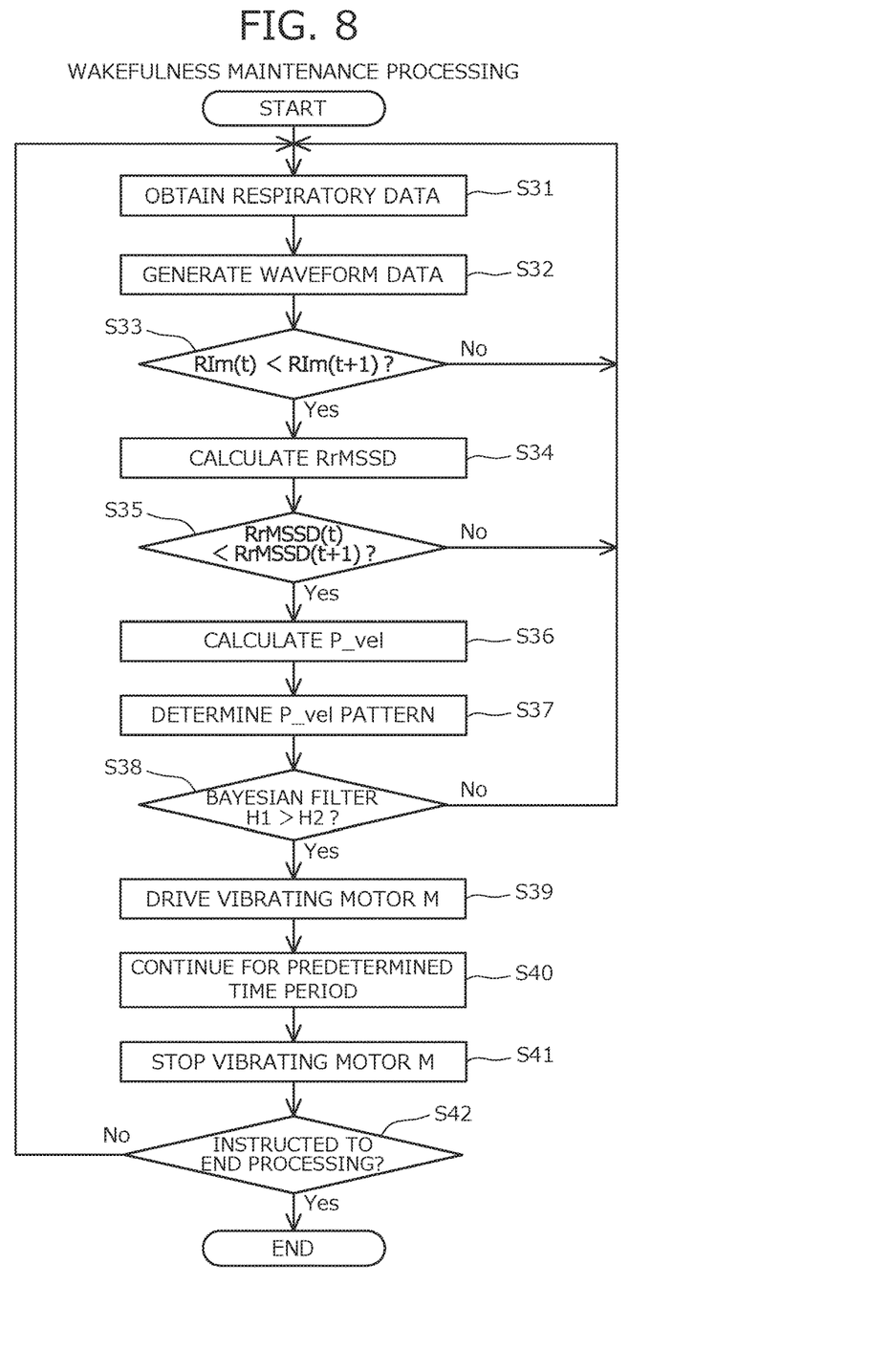
FIG. 8 is a flowchart showing an example of wakefulness maintenance processing.

Next, the wakefulness maintenance processing is described with reference to FIG. 8. FIG. 8 is a flowchart showing an example of the wakefulness maintenance processing.

Steps S31 to S38, S42 in the wakefulness maintenance processing shown in FIG. 8 are substantially the same as steps S11 to S18, S21, respectively in the wakefulness determination processing shown in FIG. 2. Therefore, in order to clarify differences, only the differences is described and other descriptions is partially omitted.

The wakefulness maintenance processing is processing in which in response to a determination result made by the foregoing wakefulness determination processing that the seated occupant is in a state of low wakefulness, the vibrating motor M is driven and thereby the seated occupant is maintained in a state of wakefulness. One of the differences of the wakefulness maintenance processing from the wakefulness determination processing is that when the condition that the seated occupant is in a state of wakefulness is satisfied (step S33: No, step S35: No or step S38: No), the processing returns to a respiratory data obtaining step (step S31) regardless of whether or not the processing termination instruction is given.

Also, in the wakefulness maintenance processing, when the determination unit 73c has determined with the Bayesian filter that the seated occupant is in a state of low wakefulness (step S38: Yes), the drive unit 73d drives the vibrating motor M (step S39). Then, the drive unit 73d allows the vibrating motor M to drive continuously for a predetermined time period, and after the seated occupant is stimulated by vibrations for a predetermined time period (step S40), the drive unit 73d stops the vibrating motor M (step S41). When the foregoing wakefulness maintenance processing has determined that the seated occupant is in a state of low wakefulness, the vibrating motor M can be driven timely and the seated occupant can be effectively maintained in a state of wakefulness.

The aforementioned embodiment describes RIm, P_vel mean, and P_vel pattern included as the data in the likelihood applied to the Bayesian filter. Alternatively, RrMSSD may be included as the data. In other words, RrMSSD values are divided into plural ranges such as data D1 and data D2, and probabilities that the values are within the respective ranges when the seated occupant is in a state of low wakefulness and probabilities that the values are within the respective ranges when the seated occupant is in a state of wakefulness may be included in the likelihood of the Bayesian filter. Alternatively, the likelihood may include any probabilities associated with data on a state of wakefulness of a person. The data on a state of wakefulness of a person may include, for example, data during driving on a highway on which there are few changes in a road situation determined with a signal from an electronic toll collection (ETC) system or data during driving in the daytime or night-time. In addition, the data configuring the likelihood may include one piece of data. If the data configuring the likelihood includes, in particular, five or six pieces of data, the accuracy of the wakefulness determination can be increased while an increase in load associated with the wakefulness determination processing is inhibited.

Also, a switch (an obtaining unit) may be provided, wherein when a seated occupant feels drowsiness or does not feel drowsiness, the switch obtains a signal (a wakefulness signal), associated with low wakefulness or wakefulness, in accordance with operation by the seated occupant and sends the signal to the controller 70. For processing with the switch and the signal, in the calculation step, the calculation unit 73b updates (sets) various conditions such as probabilities of low wakefulness or probabilities of wakefulness, which are associated with the data stored in the storage unit 72, or such as prior probabilities and adjusts the criteria for determining wakefulness. With such a configuration, the adverse influence that the wakefulness determination is wrongly made due to characteristics of individuals of seated occupants can be reduced, and the wakefulness determination can be performed highly accurately.

Further, the aforementioned embodiment describes that the waveform generation unit 73a generates the pressure waveform data of the respiration sensor and the RI waveform data but does not necessarily generate waveform data. Alternatively, the waveform generation unit 73a only has to calculate a function between a pressure signal obtained from the pressure sensor 20 and an elapsed time.

Furthermore, the aforementioned embodiment describes that in a case where the determination unit 73c has determined that the seated occupant is in a state of low wakefulness, the state is indicated on the display or the seated occupant is stimulated with the vibrating motor M; however, the present disclosure is not limited to such a configuration. For example, in a case where the determination unit 73c has determined that the seated occupant is in a state of low wakefulness, a speaker may emit an alarm sound or a light emitting device may emit light.

In the aforementioned embodiment, a vehicle seat which can be mounted on an automobile is explained as a concrete example, but other embodiments are not limited thereto. The vehicle seat of the present disclosure can be utilized as a passenger seat for an airplane, a boat, or the like. Further, the vehicle seat of the present disclosure may be applied as a seat for a movie theater or a performing theater, or a relaxation seat or may be applied to a bed or others to be touched by a person.

TABLE OF REFERENCE NUMERALS

S: vehicle seat
1: seat cushion
2: seat back
10: wakefulness-maintenance apparatus
20: pressure sensor (respiration sensor)
70: controller
  72: storage unit
  73a: waveform generation unit
  73b: calculation unit
  73c: determination unit
  73d: drive unit
M: vibrating motor

The invention claimed is:

1. A wakefulness determination method using a respiration sensor that obtains respiratory data about respiration of a person, a calculation unit that calculates the respiratory data obtained from the respiration sensor, and a controller including a determination unit that determines a state of the person, the wakefulness determination method comprising:
    obtaining, by the respiration sensor, respiratory data of the person;
    calculating, by the calculation unit, a degree of change in respiration, which is a degree of change in the obtained respiratory data per unit time; and
    determining, by the determination unit, wakefulness of the person by using a Bayesian filter where a probability of occurrence of drowsiness in the person for the degree of change in respiration is taken as a likelihood and the likelihood is multiplied by a prior probability of occurrence of drowsiness.

2. The wakefulness determination method according to claim 1, wherein the method uses an obtaining unit that obtains a wakefulness signal, which is associated with the wakefulness of the person, in accordance with operation by the person, and a storage unit that stores the wakefulness signal sent from the obtaining unit and various conditions at the time of the operation;

wherein calculating the degree of change in respiration comprises setting the likelihood or the prior probability on the basis of data stored in the storage unit.

3. The wakefulness determination method according to claim 1, wherein calculating the degree of change in respiration comprises calculating a pattern associated with a number of times that the degree of change in respiration has decreased in a predetermined time period, and the likelihood includes a probability of occurrence of drowsiness in the person for the pattern.

4. The wakefulness determination method according to claim 1, wherein calculating the degree of change in respiration comprises calculating a respiration interval (RI), which is an interval for one respiration of the person, from the respiratory data obtained from the respiration sensor, and the likelihood includes a probability of occurrence of drowsiness in the person for the RI.

5. The wakefulness determination method according to claim 1, wherein the controller includes a waveform generation unit that generates respiration interval (RI) waveform data for a respiratory waveform from the respiratory data obtained from the respiration sensor, the RI waveform data indicating transitions in a predetermined time period of a respiration interval (RI) that is an interval for one respiration of the person, in a case where a Respiration root Mean Square Successive Difference (RrMSSD) is defined by $$RrMSSD = \sqrt{\frac{\{RI(t) - RI(t-1)\}^2 + \cdots + \{RI(t+n-1) - RI(t+n-2)\}^2}{n}}$$

where the t-th RI in the RI waveform data generated by the waveform generation unit is determined as RI (t) and the n-th RI after the t-th RI in the generated RI waveform data is defined as RI (t+n), calculating the degree of change in respiration comprises calculating the RrMSSD from the RI waveform data, and the likelihood includes a probability of occurrence of drowsiness in the person for the RrMSSD.

6. The wakefulness determination method according to claim 1, wherein the likelihood includes five or six pieces of data.

* * * * *